(12) United States Patent
Sanso et al.

(10) Patent No.: US 12,002,320 B1
(45) Date of Patent: *Jun. 4, 2024

(54) MEDsafe MEDICATION DISPENSING AND MONITORING SYSTEM

(71) Applicants: David J Sanso, Morrison, CO (US); David W Sanso, Morrison, CO (US)

(72) Inventors: David J Sanso, Morrison, CO (US); David W Sanso, Morrison, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/751,719

(22) Filed: May 24, 2022

Related U.S. Application Data

(63) Continuation of application No. 16/408,185, filed on May 9, 2019, now Pat. No. 11,348,399.

(51) Int. Cl.
 *G07F 17/00* (2006.01)
 *G16H 20/13* (2018.01)

(52) U.S. Cl.
 CPC ......... *G07F 17/0092* (2013.01); *G16H 20/13* (2018.01)

(58) Field of Classification Search
 CPC .............................. G07F 17/0092; G16H 20/13
 See application file for complete search history.

(56) References Cited

U.S. PATENT DOCUMENTS

| | | | | |
|---|---|---|---|---|
| 4,573,606 A * | 3/1986 | Lewis | ................... | A61J 7/0481 221/3 |
| 5,323,929 A * | 6/1994 | Marlar | ................... | A61J 7/0481 221/121 |
| 5,472,113 A * | 12/1995 | Shaw | ................... | A61J 7/0084 221/15 |
| 5,582,323 A * | 12/1996 | Kurtenbach | .......... | A61J 7/0481 221/82 |
| 5,609,268 A * | 3/1997 | Shaw | ................... | A61J 7/0481 221/82 |
| 5,915,589 A * | 6/1999 | Lim | ...................... | A61J 7/0481 221/13 |
| 6,330,957 B1 * | 12/2001 | Bell-Greenstreet | ......................... | G07F 17/0092 221/3 |
| 6,510,962 B1 * | 1/2003 | Lim | .................... | G07F 17/0014 700/243 |
| 8,068,934 B2 * | 11/2011 | Saltsov | ................. | A61J 7/0481 221/121 |
| 11,348,399 B1 * | 5/2022 | Sanso | ................... | A61J 7/0084 |
| 2012/0006847 A1 * | 1/2012 | Coe | .................... | G06Q 20/3226 222/52 |
| 2018/0039756 A1 * | 2/2018 | Phipps | .................. | G16H 40/63 |

* cited by examiner

*Primary Examiner* — Michael Collins
(74) *Attorney, Agent, or Firm* — Luis Figarella

(57) ABSTRACT

A medication storage and dispensing system that includes a plurality of cavities that can be used to securely store and dispense pills and other medications in a secure, traceable and controlled environment. The system allows for the secure transport and dispensing, while allowing the tracking of inventory. The system provides reminders of when the medication should be taken.

4 Claims, 12 Drawing Sheets

MEDsafe MEDICATION DISPENSING AND MONITORING SYSTEM

CROSS-REFERENCE TO RELATED APPLICATIONS

This application is a continuation of pending U.S. patent application Ser. No. 16/408,185 titled "MEDsafe Medication Monitoring System", filed on May 9, 2019 the disclosure of which is herein incorporated by reference in its entirety.

PATENTS CITED

The following documents and references are incorporated by reference in their entirety, Kraft et al (WO 2013/033033), Lohman (U.S. Pat. No. 9,465,918) and Denny et al (U.S. Pat. Pub. No. 2015/0251839), Villegas Estrada (U.S. Pat. Pub. No. 2010/0147867), Schiff et al (U.S. Pat. Pub. No. 2018/0360693), Aby-Eva (U.S. Pat. Pub. No. 2014/0102859) and Baarman et al (U.S. Pat. Nos. 9,218,458 and 9,597,261).

FIELD OF THE INVENTION

The present invention relates to a system and method for the safe and authorized transport, storage and dispensing of medication, and for the access and dispensing of said medication only to approved and/or authorized parties.

DESCRIPTION OF THE RELATED ART

Over 10.3 million people used prescription opioids without a prescription in 2014. In 2016, 16 people died every day from opioid related overdoses, and 11.5 MM people misused prescription opioids. From July 2016 through September 2017 Opioid overdoses increased 30% in 45 states.

It can be difficult for doctors and health specialists to monitor patients' use of prescription drugs and supplements, particularly of opioids. Within family groups, sometimes unauthorized access to one patient's prescription by someone else, creates dangers and often illegal behavior. What is needed is a safe way in which to control, store and dispense addictive substances.

SUMMARY OF THE INVENTION

This section is for the purpose of summarizing some aspects of the present invention and to briefly introduce some preferred embodiments. Simplifications or omissions may be made to avoid obscuring the purpose of the section. Such simplifications or omissions are not intended to limit the scope of the present invention.

In one aspect the invention is about a controlled access medication dispensing system comprising a tamper-resistant (possibly tamper-proof) medication storage and dispensing unit equipped with internal medication storage and dispensing components, one or more dispensing openings and electronic interface components to control said internal medication component, including storing patient prescription, patient identification and stored medication information by authorized medical authorities or personnel. In another aspect, said dispensing units is comprised of an enclosed wheel within a housing, wherein said wheel is mechanically linked with wheel rotation components, said wheel having two or more cavities, so that rotation of said wheel by said rotation components causes the contents to come out through one or more dispensing slots. In yet another aspect, said wheel rotation components are selected from a combination of one or more of: a worm drive motor, stepper motor, servo motor, mechanical clock mechanism or such other, said rotation component is coupled to one or more gearing teeth on said wheel and said wheel can only be moved while said mechanism is engaged. In another aspect, there is a dispensing sensor on said dispensing slot. In yet another aspect, said dispensing unit is sealed.

In another aspect a control and monitoring unit having one or more user identification (ID) confirmation components, system interface electronic components and network interface components for interfacing to one or more of said dispensing units and operation of said medication dispensing and storage portion is limited to those authorized by medical authorities. In yet another aspect, said user identification (ID) confirmation components are selected from one or more of the group comprised of: biometrics for face recognition, fingerprint recognition and/or voice recognition, Global Positioning (GPS) location, Cellular/Wireless/Internet location, password entry, two factor authentication, Personal Identification Numbers (PIN) entry or authorized personnel interaction via voice/video, said system interface electronic components are selected from one or more of the group comprised of: wired or wireless electronics including power, communication and/or interface and said network interface electronic components are selected from one or more of the group comprised of: IoT, RFID, Internet protocols, Wi-Fi, Bluetooth, email, 4G, 5G, SMS text, or messaging app (e.g. Telegram, WhatsApp, etc.). In another aspect said network interface is carried over a secure channel. In yet another aspect a refilling unit configured to drop medication via the dispensing unit's slot and automatically advancing the dispensing wheel within the dispensing unit. In yet another aspect said dispensing unit is lockable and access to said medication storage portion is limited to authorized medical authorities. In yet another aspect a refilling unit configured to drop medication via the dispensing unit's slot and automatically advancing the dispensing wheel within the dispensing unit.

In another aspect, the invention is about a method for controlled access medication dispensing, said method comprising providing a tamper-resistant (possibly tamper-proof) medication storage and dispensing unit equipped with internal medication storage and dispensing components, one or more dispensing openings and electronic interface components to control said internal medication component, including storing patient prescription, patient identification and stored medication information by authorized medical authorities or personnel. In yet another aspect said dispensing units is comprised of an enclosed wheel within a housing, wherein said wheel is mechanically linked with wheel rotation components, said wheel having two or more cavities, so that rotation of said wheel by said rotation components causes the contents to come out through one or more dispensing slots. In another aspect said wheel rotation components are selected from a combination of one or more of: a worm drive motor, stepper motor, servo motor, mechanical clock mechanism or such other, said rotation component is coupled to one or more gearing teeth on said wheel and said wheel can only be moved while said mechanism is engaged. In yet another there is a dispensing sensor on said dispensing slot. In another aspect said dispensing unit is sealed. In another aspect providing a control and monitoring unit having one or more user identification (ID) confirmation components, system interface electronic components and network interface components for interfacing to one or more of said dispensing units and wherein operation of said medication dispensing and storage portion is limited to those authorized by medical authorities.

Other features and advantages of the present invention will become apparent upon examining the following detailed description of an embodiment thereof, taken in conjunction with the attached drawings.

Figure 1:
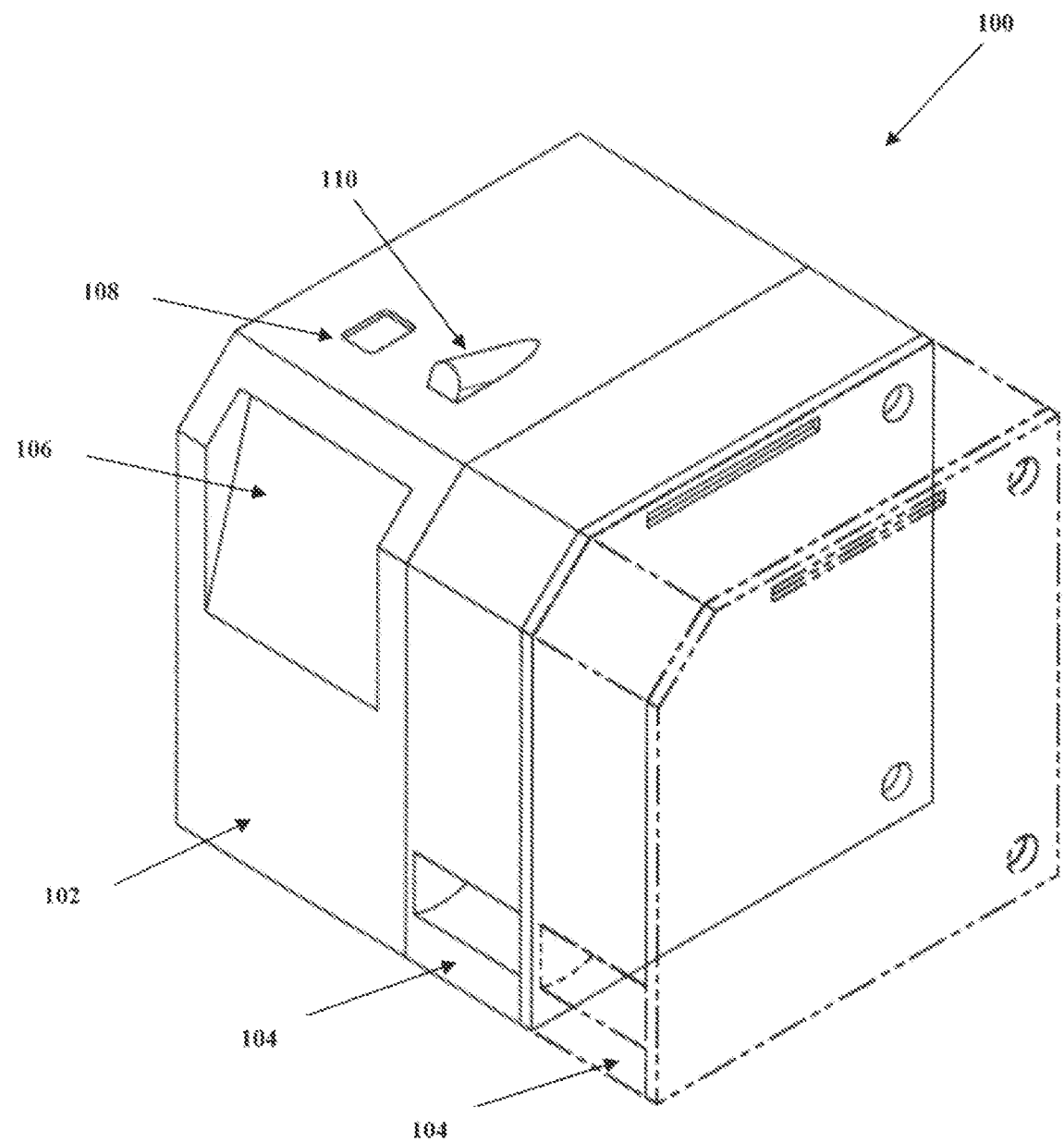
FIG. 1 shows an overall view of a proposed Medsafe monitoring system, according to an exemplary embodiment of the invention.

The above-described and other features will be appreciated and understood by those skilled in the art from the following detailed description, drawings, and appended claims.

DETAILED DESCRIPTION OF THE PREFERRED EMBODIMENT

This section is for the purpose of summarizing some aspects of the present invention and to briefly introduce some preferred embodiments. Simplifications or omissions may be made to avoid obscuring the purpose of the section. Such simplifications or omissions are not intended to limit the scope of the present invention.

To provide an overall understanding of the invention, certain illustrative embodiments and examples will now be described. However, it will be understood by one of ordinary skill in the art that the same or equivalent functions and sequences may be accomplished by different embodiments that are also intended to be encompassed within the spirit and scope of the disclosure. The compositions, apparatuses, systems and/or methods described herein may be adapted and modified as is appropriate for the application being addressed and that those described herein may be employed in other suitable applications, and that such other additions and modifications will not depart from the scope hereof.

Simplifications or omissions may be made to avoid obscuring the purpose of the section. Such simplifications or omissions are not intended to limit the scope of the present invention. All references, including any patents or patent applications cited in this specification are hereby incorporated by reference. No admission is made that any reference constitutes prior art. The discussion of the references states what their authors assert, and the applicants reserve the right to challenge the accuracy and pertinence of the cited documents. It will be clearly understood that, although a number of prior art publications are referred to herein, this reference does not constitute an admission that any of these documents form part of the common general knowledge in the art.

As used in the specification and claims, the singular forms "a", "an" and "the" include plural references unless the context clearly dictates otherwise. For example, the term "a transaction" may include a plurality of transaction unless the context clearly dictates otherwise. As used in the specification and claims, singular names or types referenced include variations within the family of said name unless the context clearly dictates otherwise.

Certain terminology is used in the following description for convenience only and is not limiting. The words "lower," "upper," "bottom," "top," "front," "back," "left," "right" and "sides" designate directions in the drawings to which reference is made, but are not limiting with respect to the orientation in which the modules or any assembly of them may be used.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

Figure 2:
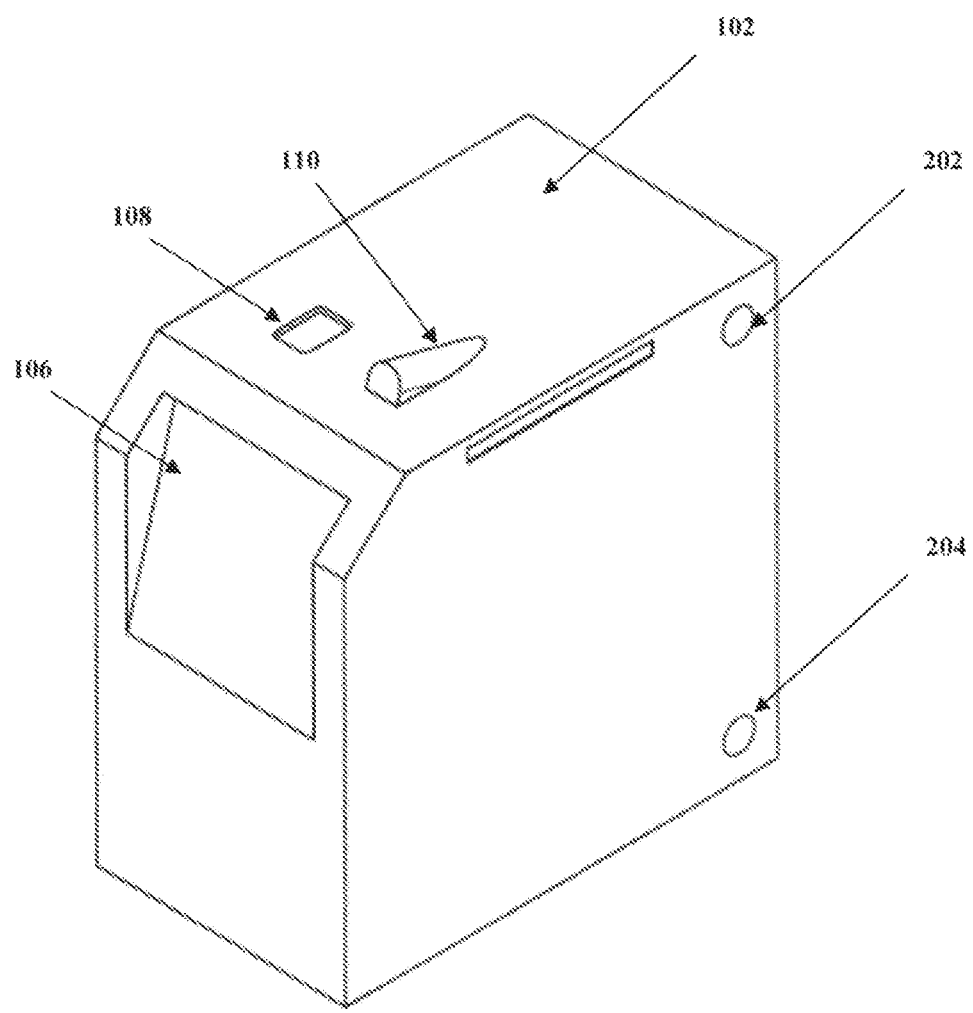
FIG. 2 shows the two primary components of a proposed Medsafe monitoring system, according to an exemplary embodiment of the invention.

Referring to FIGS. 1-2 we see an overall view 100 of a proposed Medsafe monitoring system, comprised of a primary control unit 102 and one or more medication storage and dispensing units 104. The combination of both units 102/104 provides a secure, tamper-proof system that allows for the distribution, storage and secure dispensing of one or more medications.

The MEDsafe Lifesaver would allow for distribution of medication (in all forms including pills, pill packs, tablets, envelopes (containing both solids, gels or even liquids), dispensers, aspirators, etc.) through a secure, tamper-proof medication storage and dispensing unit 104, which will dispense individual doses sequentially only after strict user identification (ID) requirements are met through the use of one or more ID establishing components in the control unit 102. These user ID requirements may include components capable of establishing and/or confirming user biometrics (including but not limited to ID determination for Face recognition, fingerprint, voice recognition and others), Global Positioning (GPS) location, as well as through cellular/wireless internet location, and traditional security such as passwords, two factor authentication, Personal Identification Numbers (PIN), authorized medical personnel approval after voice/video interaction and others. Each dispensed dose will be tracked and logged (including time and frequency), in order to decreasing both access and medication misuse.

The above may be accomplished through a user interface screen or combination screen/keypad 106, a fingerprint scanner 108, a camera 110 and speaker/microphone (built anywhere convenient within the control unit 102. One or more computer processors and memory electronics network interface components are also built within the unit 102, including internet of things (IoT) interface electronics (including but not limited to Radio Frequency Identification (RFID), Internet awareness (including Internet Interface I/F, network identification, messaging, email, website I/F, etc.), as well as programming so the device may be interfaced to via Wi-Fi, Bluetooth, Wireless Internet (such as 4G, 5G and other wide area protocols), WhatsApp, SMS messaging, Facebook Messaging, etc. In one embodiment, the control and/or dispensing units may be externally powered and/or have internal energy storage components (batteries, backup batteries, etc.).

The central unit 102 may be configured to allow medication tracking and/or reordering using a network. The network may be the Internet or some other network allowing for communication between the system 100 and an ordering/reordering/dispensing facility (e.g. a pharmacy, medical dispensing facility, authorized medication dispensary, etc.). In addition to reordering, the time and day of each medication dispensing may be logged and communicated to a medical supervising authority (such as Pharmacist, Pharmacist Assistant, Physician, hospital or insurance company or any such legally authorized medication dispensing entity).

In one embodiment, the central unit 102 has a touch screen 106 that allows a user to navigate through a graphical user interface that control operation of the dispenser system 104 and related functions. The user interface may include automated operation (via Biometrics, etc., or PIN, or password), or it may require video/voice interface with a supervisory agent across the internet and/or telephonic network.

The control unit 102, is thus a stand-alone unit capable of interfacing both with the user, as well as the user's portable electronics such as cellphone, smartphone, Tablet, Personal Computer (PC), terminal, Smartwatch, etc. AND with a medical dispensing control organization (e.g. Pharmacy, Medical Plan, Doctor's Office, Legal Authorities or their proxies, etc.). In this fashion, the control unit 102 acts as an interface medium to the authorized device user or patient. Utilizing a secure network, the control unit will transmit patient usage information to a central database within the cloud, keeping track of the time of day and amount dispensed will greatly help in the ability for institutions to understand and develop new pain management protocols. In one embodiment, the interface and communication between the control unit 102 and the one or more dispensing units 104, and/or the interface and communication between the control unit 102 and any remotely located supervisory/management entities (e.g. pharmacist, nurses, doctors and others) is over a secure channel.

Figure 3:
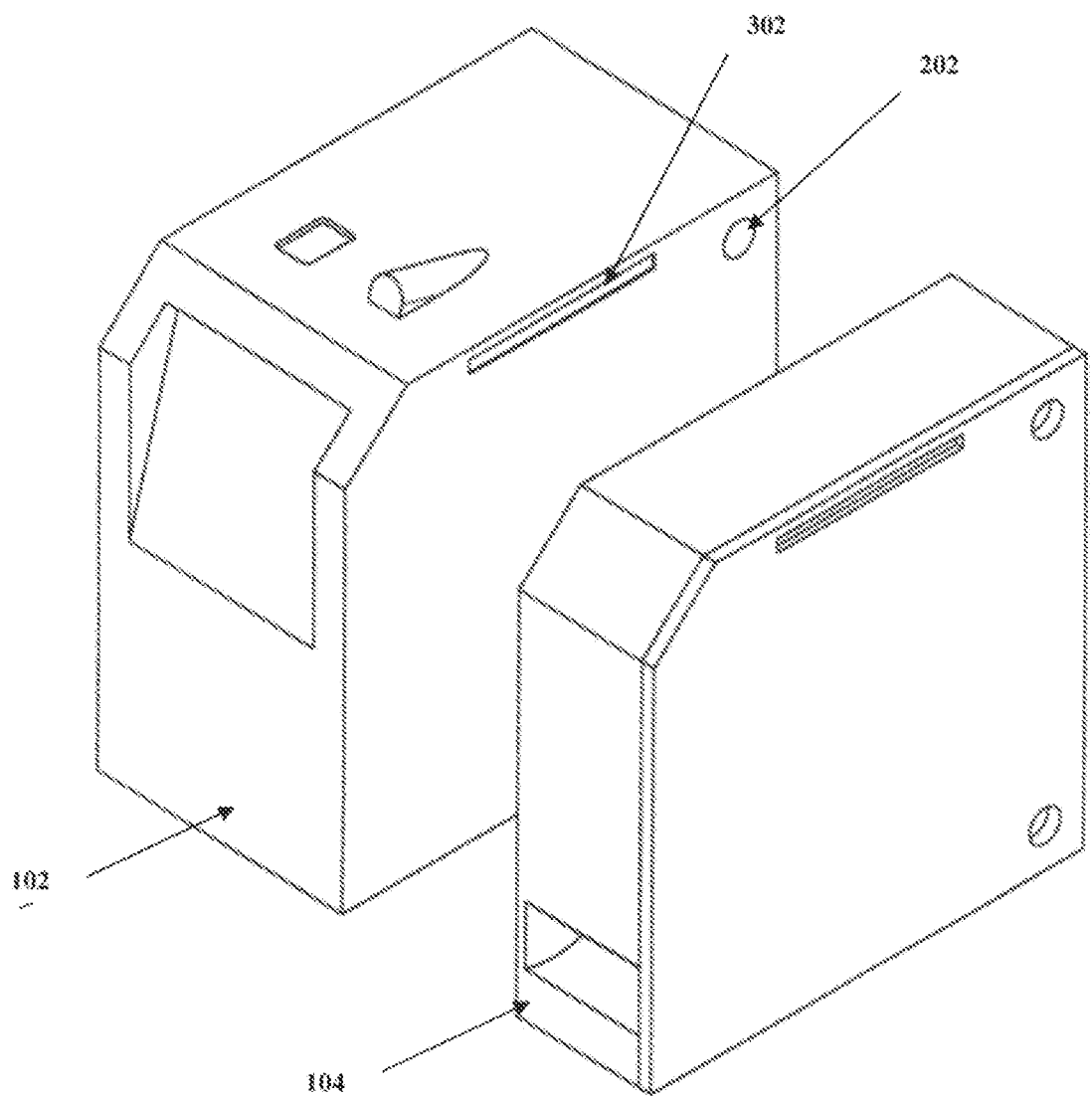
FIG. 3 shows the control unit of a proposed Medsafe monitoring system, according to an exemplary embodiment of the invention.
Figure 4:
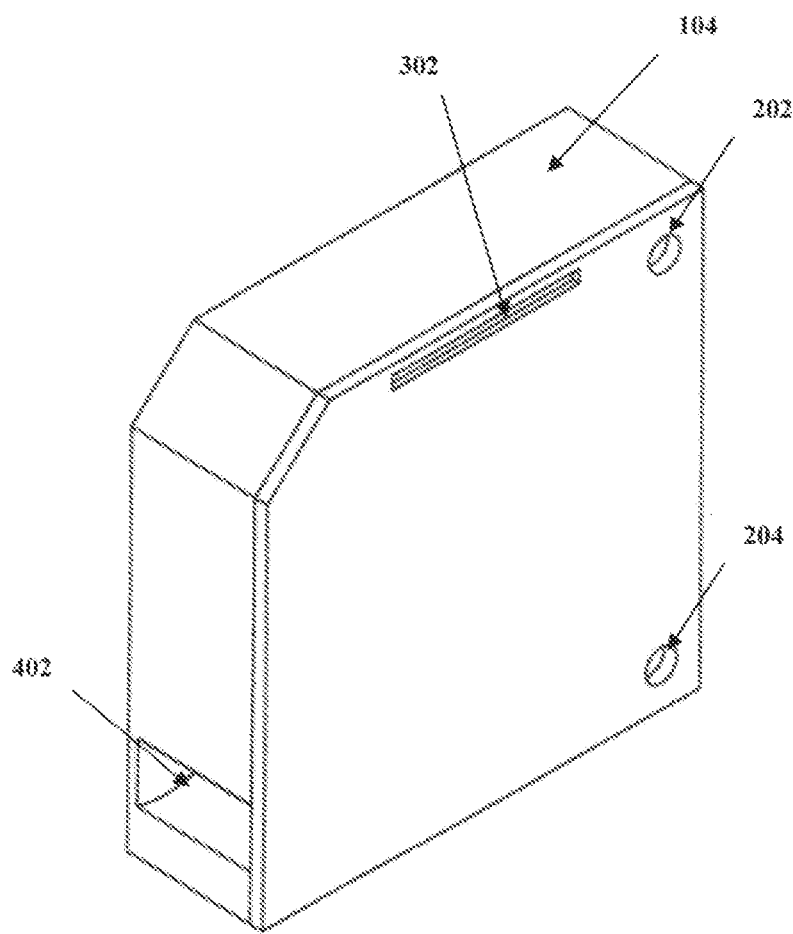
FIG. 4 shows a storage and dispensing unit of a proposed Medsafe monitoring system, according to an exemplary embodiment of the invention.
Figure 5:
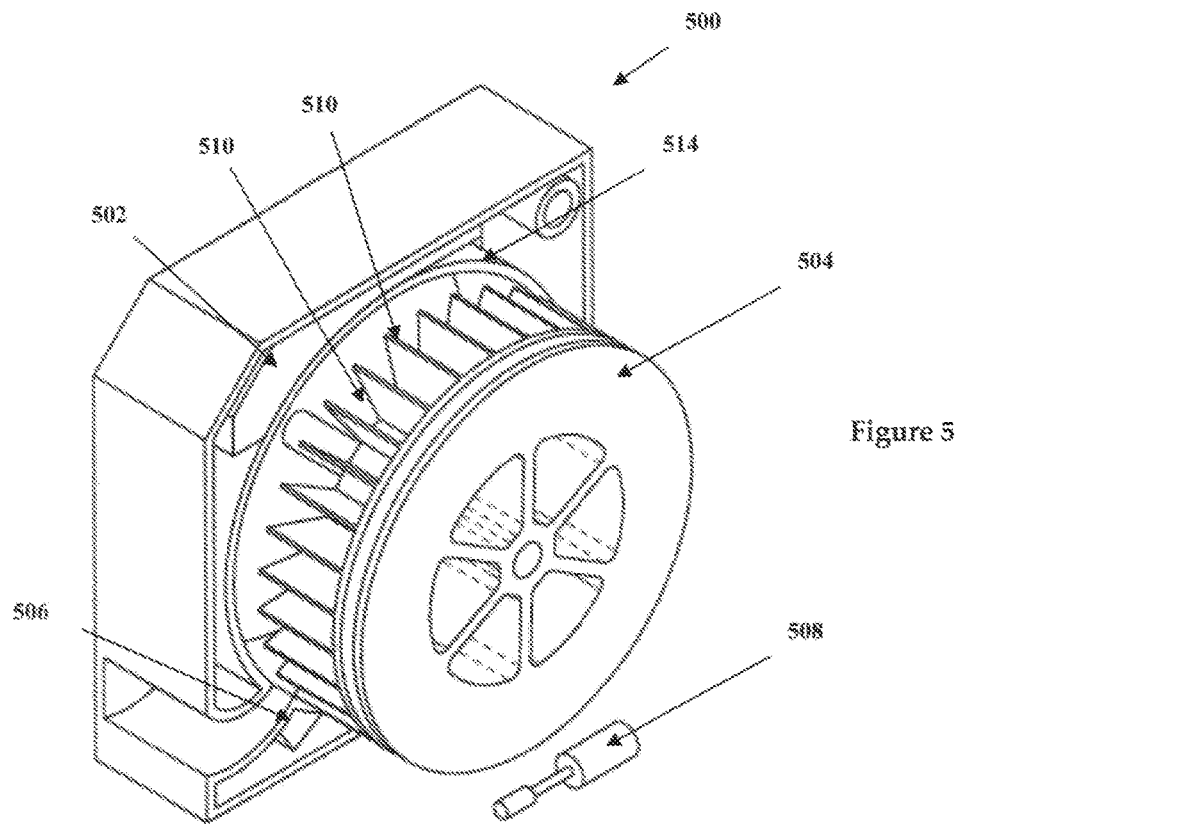
FIG. 5 shows an exploded interior view of a proposed Medsafe monitoring system, according to an exemplary embodiment of the invention.
Figure 6:
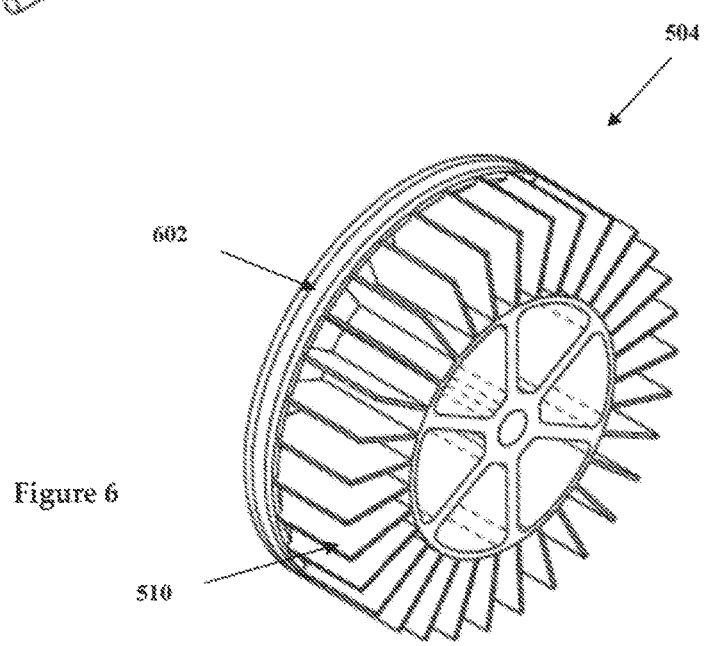
FIG. 6 shows details of the dispensing wheel of a proposed Medsafe monitoring system, according to an exemplary embodiment of the invention.
Figure 7:
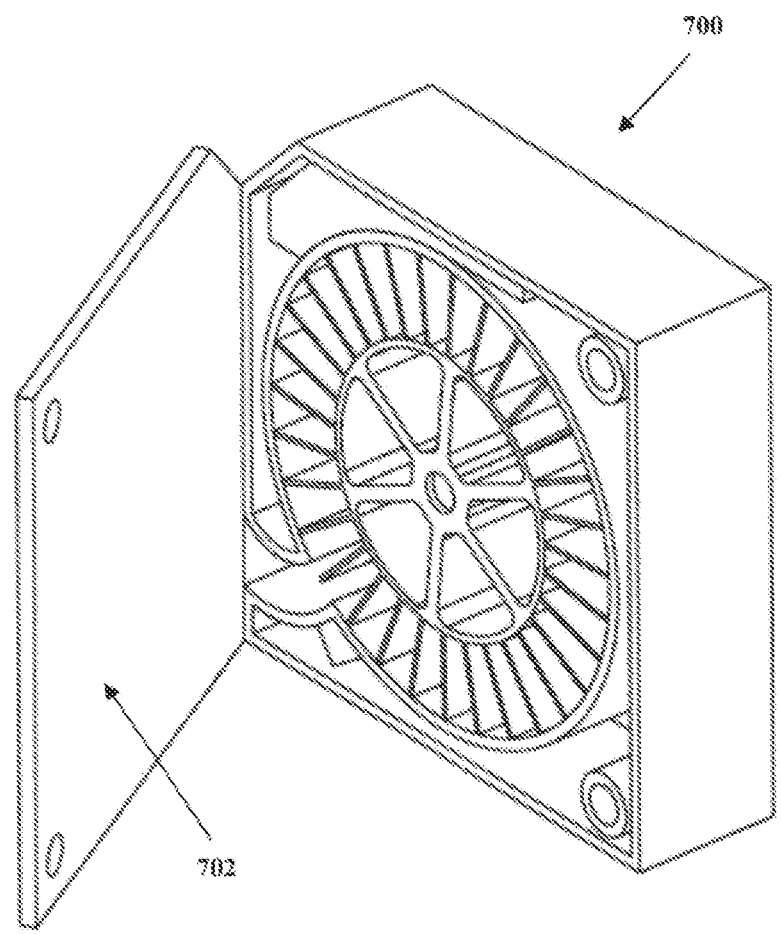
FIG. 7 shows an internal view of a proposed Medsafe monitoring system, according to an exemplary embodiment of the invention.
Figure 8:
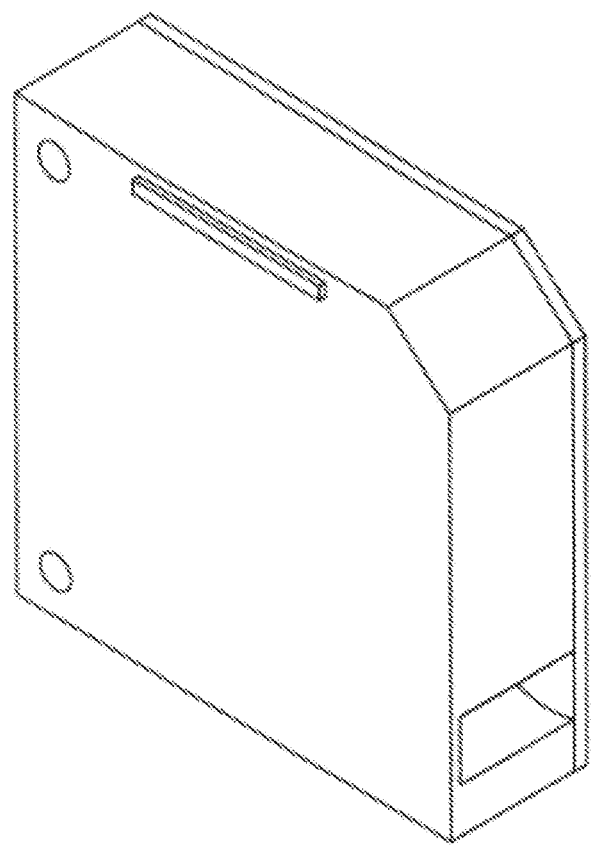
FIG. 8 shows a side view of a proposed Medsafe monitoring system, according to an exemplary embodiment of the invention.

FIGS. 3-4 illustrates the interface between the control unit 102 and the transporting/storage/dispensing unit 104. One or more guide pins, locking mechanism or alignment fixtures 202/204 are used to align the units to each other, and one or more system interface electronic components 302 are used to connect the control 102 to the one or more dispensing units 104. These system interface electronics may be wired or wireless and may include simple power (both directly connected via wiring and/or induced voltage receiver (by-passing the need to connect) for power and/or battery recharging and/or combinations thereof. Similarly, the wiring may be used for electronic signal transfer (e.g. USB, Firewire and other Interfaces), as well wireless communication between the control unit 102 and the dispensing units 104, such as Wi-Fi, Bluetooth and others. In one embodiment, the dispensing unit 104 is designed to be sealed (with only the primary opening having access to the interior) and tamper-proof, so that it may be even shipped via postal/courier service while filled with high value/risk prescriptions.

The profile for one or more patients is entered/confirmed onto the control unit, and it is coupled with the unique ID of the one or more dispensing units 102 (say a 1$^{st}$ one for one patient and a second for another). Thus in one embodiment, the patient takes a secured and/or locked medication dispensing tray 104 home, and then coupled electrically and/or electronically to the control unit 102.

Figure 11:
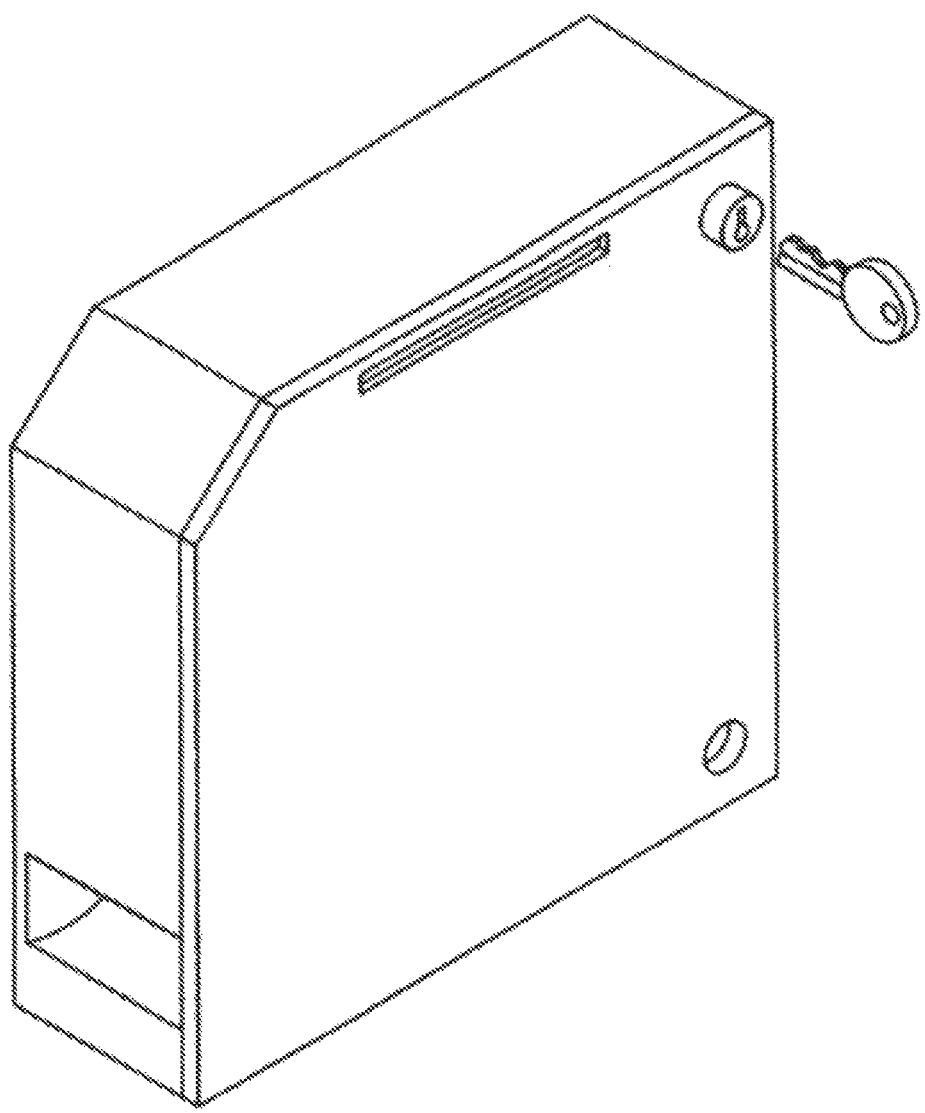
FIGS. 11 and 12 show proposed all-in-one Medsafe monitoring systems, according to exemplary embodiments of the invention.
Figure 12:
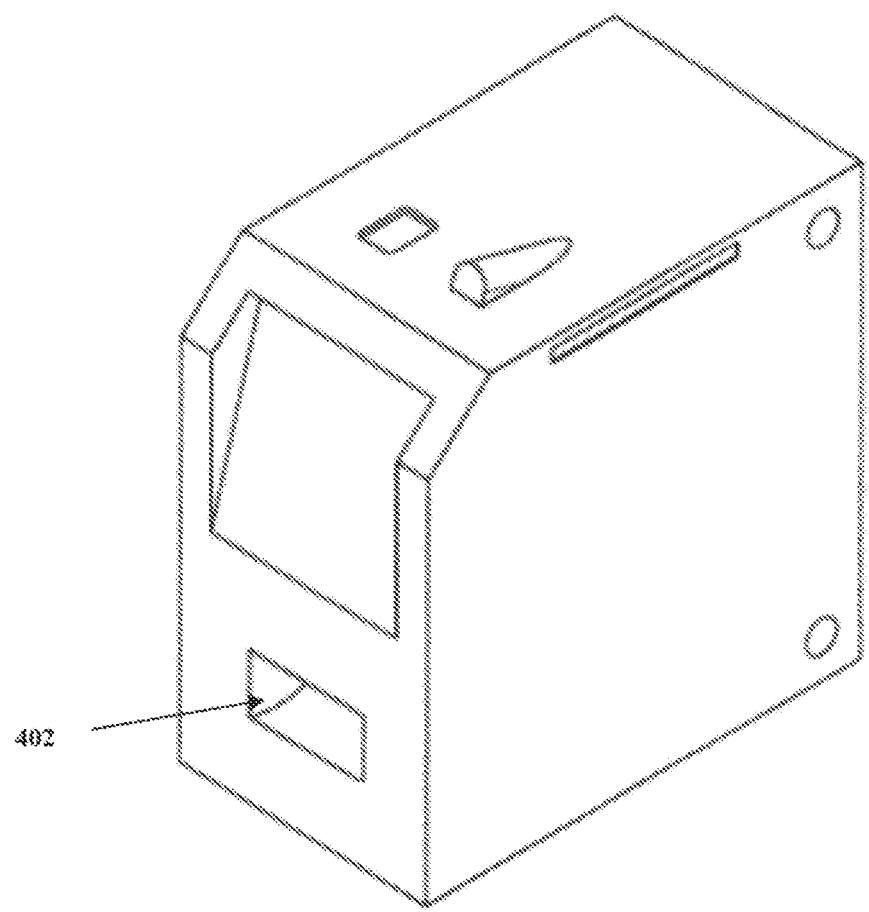

In one embodiment, once the user is authenticated (via video call, biometric validation, password or other suitable form) by validating the patient, the drug and the medication dosage, the dispensing unit 104, proceeds to be activated and the medication is dispensed via the opening or dispensing slot 402. In one embodiment 100, this is accomplished by mating the dispenser 104 to the control unit 102, in another, this is accomplished by having the dispensing unit be also the control unit FIG. 12. In yet another embodiment, the control unit 102 is an app within a Smartphone that is connected via wireless to the dispensing unit 104 such as FIG. 11 so that validation of the user is carried out through the screen, camera and biometrics/authentication components connected to the phone. In addition, we see a lockable case 204 and key. In all cases above, no dispensing is done without satisfying the medical authorities and their approved proxies/delegates.

FIGS. 5-8 illustrate the internals of the dispensing unit 104, which include dispensing electronics 502 which control the rotation of the dispensing wheel 504. The wheel 504 has two or more cavities 510 formed by the paddles 512 along it's periphery. Said wheel 504 is housed, surrounded, enclosed within a cylinder 514, the cavity forms a sealed void which is only accessible to the outside when lined up with the dispensing slot or opening 402. That is, the medication will stay within the cavity until the wheel rotates and aligns with it, at which point it drops via gravity 700.

In one embodiment, there is a dispensing sensor 506, so that there may be a positive detection of the cavity's content flowing outbound via the slot 402. The wheel 504 is advanced via a control signal from the electronics 502 which activate wheel rotation components. Said wheel rotation components may be comprised of one or a combination of electrical, pneumatic, spring or other suitable motors or actuator. In one embodiment, a worm drive motor 508 coupled (FIG. 6) to a set of gearing teeth 602 along the periphery is preferred, since those skilled in the art will appreciate that a worm drive is very hard to move through mechanical 'pushing' by fingers or other tools via the slot 402. (Something that users or others may attempt to do in order to obtain an unauthorized dose).

Do note, that the worm drive does not preclude the operation of the wheel 504 in either direction, something that may be advantageous when refilling a wheel that has some medication left in it. Similarly, one or more portions of the sides 702 of the dispensing unit 104 may be made translucent or transparent, so that the number of wheel 504 slots 510 still having medication may be ascertained.

In one embodiment, the dispensing unit 104 may have one or more sides openable 702 via keys or locks, or even via an internal lock that only releases under the acknowledgement of an authorized medical authority. This would provide a tamper-proof enclosure 104. In another embodiment, the dispensing unit 104 be sealed, so that access to the interior is controlled through the one or more entries (the slot 402) for both entry and exit of the medications.

Figure 9:
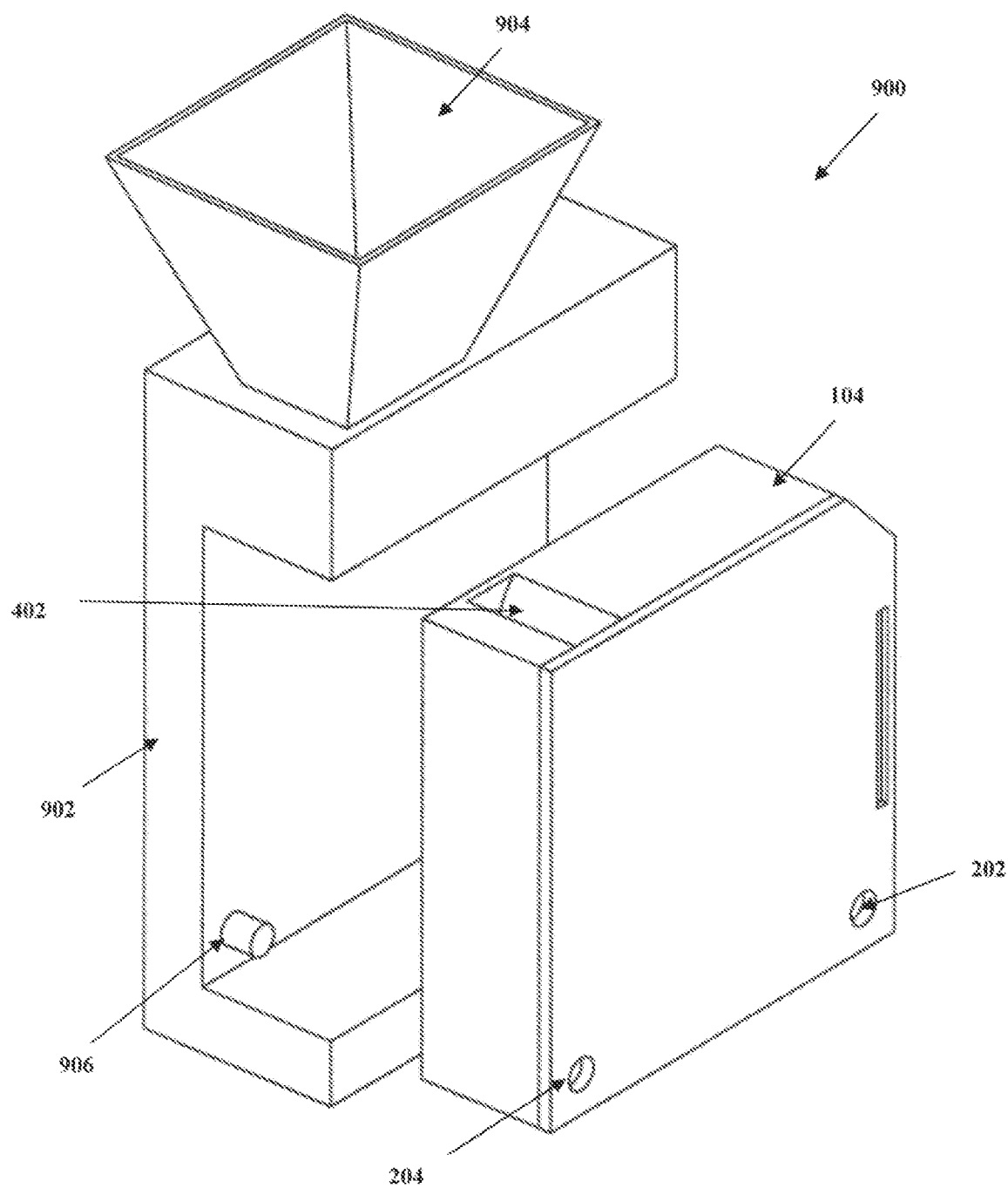
FIG. 9 shows a perspective view of a proposed re-filling unit, according to an exemplary embodiment of the invention.
Figure 10:
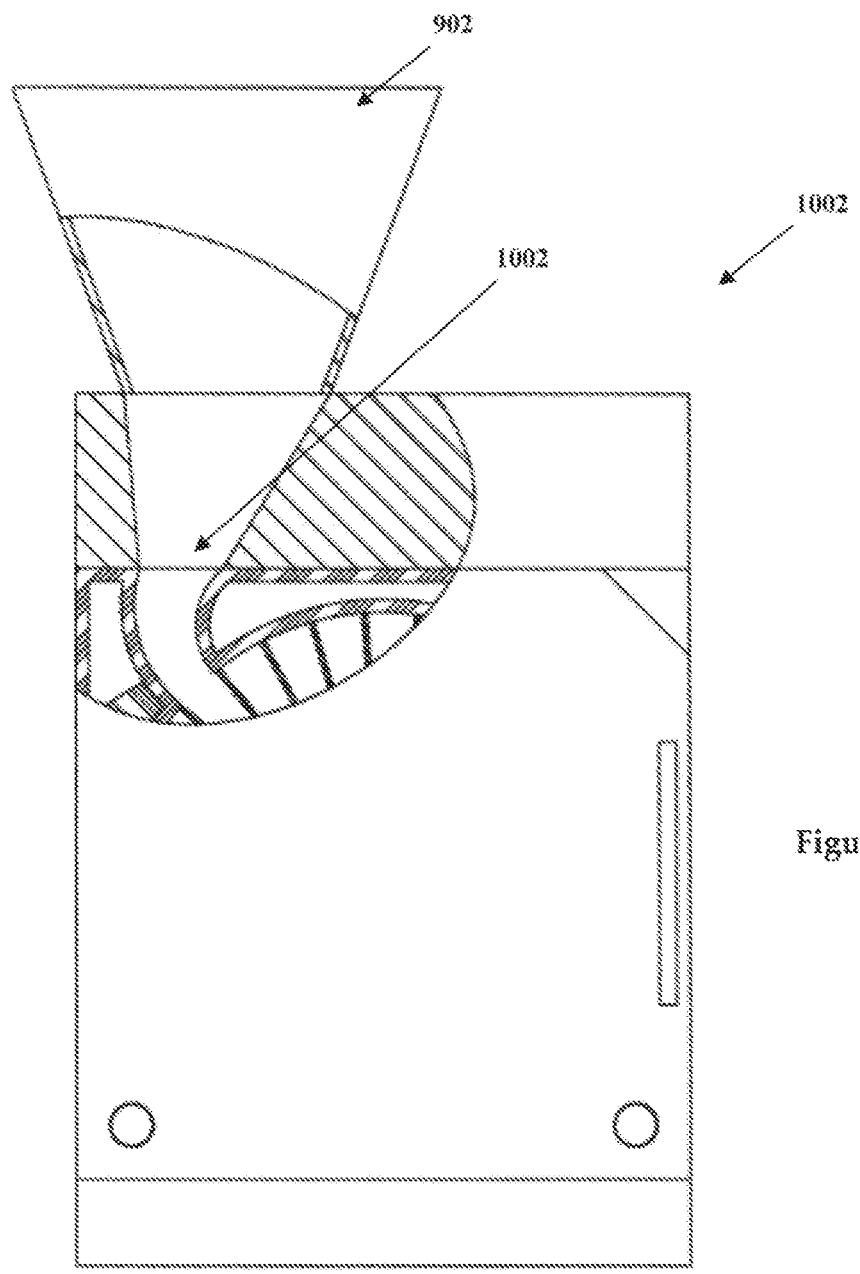
FIG. 10 shows a side view of a proposed re-filling unit, according to an exemplary embodiment of the invention.

FIGS. 9-10 illustrate a proposed refill solution 900. In this, an authorized entity (pharmacy, medical distributor or logistic agency such as Amazon) need only reverse the process of filling. That is, have a special control unit 902 programmed to control a dispensing unit 104 that is nested within it (via the alignment of fixture(s) 906 to fixture 202/204) so that the feeding the hopper 904 with medication, results in the medication dropping into the cavity. In one embodiment, the passing of the medication into the cavity is noticed by the sensor 506 within the dispensing unit 104, and the load control unit 902 advances the wheel 504. In another embodiment 1000, a sensor 1002 is mounted within the hopper 902 to confirm/detect the medication entry into the dispensing unit 104. The wheel 504 every time the appropriate cavity load (typically a prescription dose) receives the dose. This may be detected via an external sensor 1002, or via the confirmation from the internal sensor 506.

In an alternate embodiment, where live monitoring is required/desired, once the patient submits their biometrics to the unit 102, there is an additional step where the provider will verify through telemedicine the patient ID/information/person and dispense the medication via a secure network.

Figure 13:
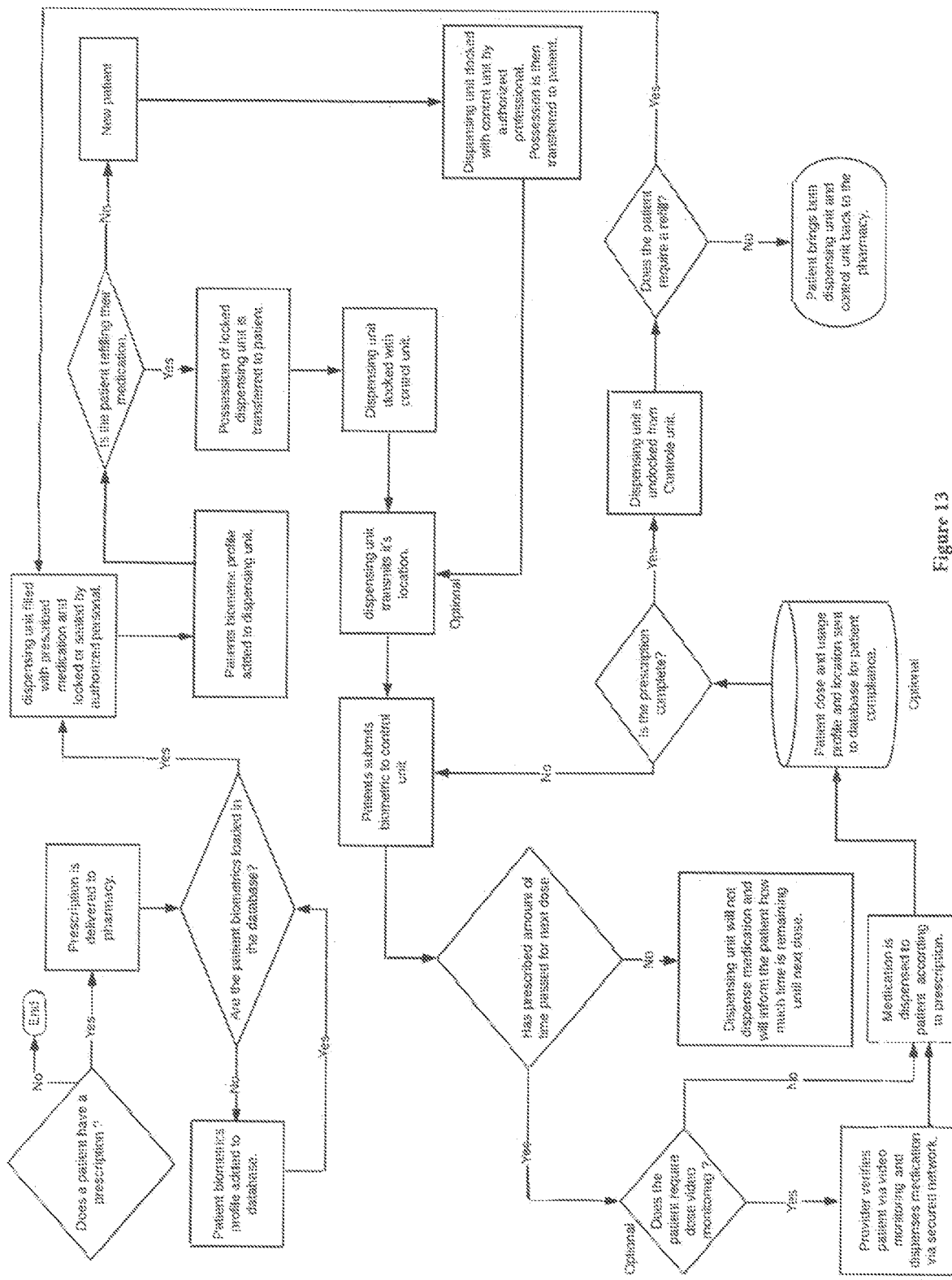
FIG. 13 shows a flowchart of the system operation, according to an exemplary embodiment of the invention.

FIG. 13 illustrates the flowchart of a proposed embodiment, showing the system operation. Any attempt to access medication outside of prescriber's intention will automatically be transmitted to the provider, including the biometrics of anyone that has attempted to open the unit 102 but has failed to be authenticated. Even for registered patients, if the patient does not have a prescription in the system, we see the process end.

While presently dispensing and distribution of certain medication is limited to licensed pharmacies, it is interesting to see how the delivery of even licensed medications could be expanded by the use of the dispensing unit 104 proposed. Services such as AMAZON LOCKERS could be used to ensure that the dispensing unit 104 is positively delivered to the authorized user, who would still be limited to access the medication within the unit to the approved biometric/visual/PIN/password channels.

In an exemplary embodiment of the invention, the control unit 102 controls the dispensing of controlled pharmaceutical agents within the tamper-proof dispensing unit 104 located in a remote location, so that the medication is not available to the patient all at once, but dispensed directly to the patient as prescribed by the physician and only available to that patient at the time and dosage interval prescribed. For certain patients, the process may be biometric but not monitored in real time (although all deliveries are logged in time). In these, dispensing requires a biometric date from the patient to assure the prescribed pharmaceutical agent is only delivered to that patient and in the dose prescribed on the allowable dates and/or the allowable intervals for a given prescription.

In an alternate embodiment, every delivery to the patient is monitored through video as well as through biometrics, so that conditions may be judged and/or recorded. Both the control unit 102 and the dispensing unit 104 are strong enough to prevent unauthorized tampering, as well as to demonstrate any tampering with them. In this fashion, when the uniquely identified dispensing units 104 are sent back/forth to the pharmacy/dispensary, they are scanned for unauthorized access attempts.

By having the ability for the controlled administering and monitoring of controlled pharmaceutical agents through secure channels for compliance and tamper detection, unauthorized opening is both prevented and recorded with legal repercussions. The information/data about the person operating the device and/or receiving the dispensed dose is received over a secure data channel for the purpose of modifying the time or dosage by the prescribing physician.

In one embodiment, the device has video/audio capabilities, so that the identify and actions of the patient, and their compliance with any instructions can be monitored in real and/or delayed mode. This provides a method for preventing unauthorized dispensing of a controlled substance by matching patient biometric data with the prescription.

In one embodiment, the invention allows for the secure transportation, including shipping of the container having the medication to the patient, who can then, using pre-stored biometrics have the device dispense the medication. In another, the device is registered to the user biometrics' when in audio/video communication with an authorized agent, and/or when in the presence of license/authorized personnel.

Notice when we say biometrics, we refer to fingerprint, facial recognition, voice or sound recognition, and/or any other method in which we can uniquely identify a human being. In addition to recording the correct ID, the unit will record the times and identities of any failed access (be it because the person's ID fails, too many attempts. Off-times and/or other unauthorized access attempts.

In an alternative embodiment, the system may be provided with security features to help limit unauthorized or inappropriate dispensing of medication. As such, the system establishes the ID of the person operating it, so as to prevent unprescribed users from having medication delivered to them. The medication placed within the cavities 502 may be pre-packaged in child safe (or child resistant) form. When ANY tampering or dubious access attempts are recorded, the control unit 102 may be configured so as not to dispense a medication dose until the appropriate measures are taken to reactivate the unit.

The dispenser unit 104 may have an RFID ID chip, to ensure that the unit is recognized by the control unit 102. The system may have the ability to key a specific electronic device, such as a cell phone, to a specific user and the dispenser system may require the electronic device to be within proximity of the dispenser system before dispensing medication for that user. The dispenser system may determine the proximity of the keyed electronic devise using capabilities associated with Bluetooth, Wi-Fi, Near Field Communications or other wireless methods and apparatus. For example, during set up, a user may be keyed to a specific smart phone. The dispenser system may be configured to search for the smart phone to be within sufficient proximity before dispensing any pills.

To better illustrate the many applications of the system, we illustrate a one exemplary embodiment in the example below:

Example 1

1. A patient arrives at the pharmacy with a prescription for a controlled substance that requires further protection.

2. The patient's profile is applied to the prescription by the pharmacist. If the patient profile does not exist patient biometrics are added to system, by an authorized person.

3. Once patient biometrics are verified the pharmacist will fill the dispensing unit 104 with the medication for the prescription, or a unit 104 may have been previously loaded.

4. Patient biometrics and patient profile are added to the memory on both the cloud and the dispensing unit electronics 104.

5. Once the dispensing unit 104 is interfaced to the control unit 102, the information is either confirmed via the web/cloud, or the information within the dispensing unit is confirmed with that held in the control unit 102.

6. Once the patient is ready for their first dose or subsequent doses, they will submit their biometrics to the device for authentication.

7. The device will determine whether or not adequate amount of time has passed for the patient to receive their next dose. If the dose is not ready, it will indicate how much time remains before the patient is allowed to access their next dose. If an adequate amount of time has passed it will automatically dispense the prescribed amount of medication.

8. If further monitoring is needed, video confirmation will prompt the patient to submit their patient biometrics to the device, which will in turn submit the patient profile to a telemedicine provider and the telemedicine provider will be able to dispense a does by a secure network to the patient.

9. Patient use statistics will be sent to a database by a secure network in order to better monitor medication compliance for better pain management and future medication protocols.

10. Once the prescription time comes near an end, or has ended, the control unit 104 automatically notifies the cloud and the process is repeated.

11. The patient will bring either the dispensing unit 104 back to the pharmacy to be refilled, or bring the entire medication delivery system back to the pharmacy so that the unused medication is not allowing it to be disseminated illegally.

14. Once the medication tray and/or medication dispenser have been received by the pharmacy, the pharmacy will be able to repeat step one in order to determine whether or not a refill is required or the prescription has been completed.

CONCLUSION

In concluding the detailed description, it should be noted that it would be obvious to those skilled in the art that many variations and modifications can be made to the preferred embodiment without substantially departing from the principles of the present invention. Also, such variations and modifications are intended to be included herein within the scope of the present invention as set forth in the appended claims. Further, in the claims hereafter, the structures, materials, acts and equivalents of all means or step-plus function elements are intended to include any structure, materials or acts for performing their cited functions.

It should be emphasized that the above-described embodiments of the present invention, particularly any "preferred embodiments" are merely possible examples of the implementations, merely set forth for a clear understanding of the principles of the invention. Any variations and modifications may be made to the above-described embodiments of the invention without departing substantially from the spirit of the principles of the invention. All such modifications and variations are intended to be included herein within the scope of the disclosure and present invention and protected by the following claims.

The present invention has been described in sufficient detail with a certain degree of particularity. The utilities thereof are appreciated by those skilled in the art. It is understood to those skilled in the art that the present disclosure of embodiments has been made by way of examples only and that numerous changes in the arrangement and combination of parts may be resorted without departing from the spirit and scope of the invention as claimed. Accordingly, the scope of the present invention is defined by the appended claims rather than the foregoing description of embodiments.

The invention claimed is:

1. A controlled access medication dispensing system comprising;
   a tamper-resistant medication storage and dispensing unit equipped with internal medication storage and dispensing components, wherein said medication storage and dispensing unit is comprised of an enclosed wheel within a housing having only one single opening to the outside, and said wheel is mechanically linked with wheel rotation components;
   said wheel having two or more cavities, so that rotation of said wheel by said wheel rotation components causes no more than two one said cavities at a time to align with a smooth surfaced, no sharp angles and unobstructed medication chute connected directly to said single outside opening in said unit;
   said single opening providing access for loading medication into said dispensing unit's interior, as well as for dispensing medication outside said dispensing unit's interior and electronic interface components to control said internal medication component, including storing patient prescription, patient identification and stored medication information by authorized medical authorities or personnel;
   said wheel rotation components are selected from a combination of one or more of:
   a worm drive motor, stepper motor, servo motor, mechanical clock mechanism or such other;
   said wheel rotation component is coupled to one or more gearing teeth on said wheel; and
   said enclosed wheel can only be moved while said wheel rotation component is engaged;
   there is a dispensing sensor on said dispensing chute;
   said housing is sealed; and
   a refilling unit configured to drop medication via said dispensing unit's opening and automatically advancing the dispensing wheel within the dispensing unit.

2. The system of claim 1 further comprising;
   a control and monitoring unit having one or more user identification (ID) confirmation components, system interface electronic components and network interface components for interfacing to one or more of said dispensing units; and
   operation of said medication dispensing and storage portion is limited to those authorized by medical authorities.

3. The system of claim 2 further comprising;
   said user identification (ID) confirmation components are selected from one or more of the group comprised of:
   biometrics for face recognition, fingerprint recognition and/or voice recognition, Global Positioning (GPS) location, Cellular/Wireless/Internet location, password entry, two factor authentication, Personal Identification Numbers (PIN) entry or authorized personnel interaction via voice/video;
   said system interface electronic components are selected from one or more of the group comprised of:
   wired or wireless electronics including power, communication and/or interface; and
   said network interface electronic components are selected from one or more of the group comprised of:

IoT, RFID, Internet protocols, Wi-Fi, Bluetooth, email, 4G, 5G, SMS text, or messaging app (e.g., Telegram, WhatsApp, etc.).

4. The system of claim 3 wherein;
said network interface is carried over a secure channel.

\* \* \* \* \*